US005756702A

United States Patent [19]
Lohman et al.

[11] Patent Number: 5,756,702
[45] Date of Patent: May 26, 1998

[54] DETECTION OF NUCLEIC ACIDS IN CELLS BY THERMOPHILIC STRAND DISPLACEMENT AMPLIFICATION

[75] Inventors: Kenton L. Lohman, San Jose; Natalie V. Ostrerova, Mountain View, both of Calif.; Mark Van Cleve; Robert Alan Reid, both of Durham, N.C.

[73] Assignee: Becton, Dickinson and Company, Franklin Lakes, N.J.

[21] Appl. No.: 781,432

[22] Filed: Jan. 10, 1997

Related U.S. Application Data

[63] Continuation of Ser. No. 531,747, Sep. 21, 1995, Pat. No. 5,631,147.
[51] Int. Cl.[6] .......................... C07H 21/02; C07H 21/04
[52] U.S. Cl. ........................ 536/24.33; 536/23.1
[58] Field of Search ............................... 435/6; 536/22.1, 536/23.1, 24.33

[56] References Cited

U.S. PATENT DOCUMENTS 5,550,025  8/1996  Walker ................................. 435/6
5,631,147  5/1997  Lohman et al. ................. 435/911.2

*Primary Examiner*—Eggerton A. Campbell
*Attorney, Agent, or Firm*—Donna R. Fugit

[57] ABSTRACT

Thermophilic Strand Displacement Amplification (tSDA) for amplification of nucleic acid target sequences in situ in cells in suspension, on slides or in tissues is described. Excellent specimen morphology is preserved, and either DNA targets, RNA targets, or both may be selectively amplified. In situ amplification by tSDA is compatible with immunochemical techniques, so that both amplification of target sequences and immunological staining can be performed on the same specimen.

4 Claims, 1 Drawing Sheet

FIG-1A  HLA DNA AMPLIFICATION
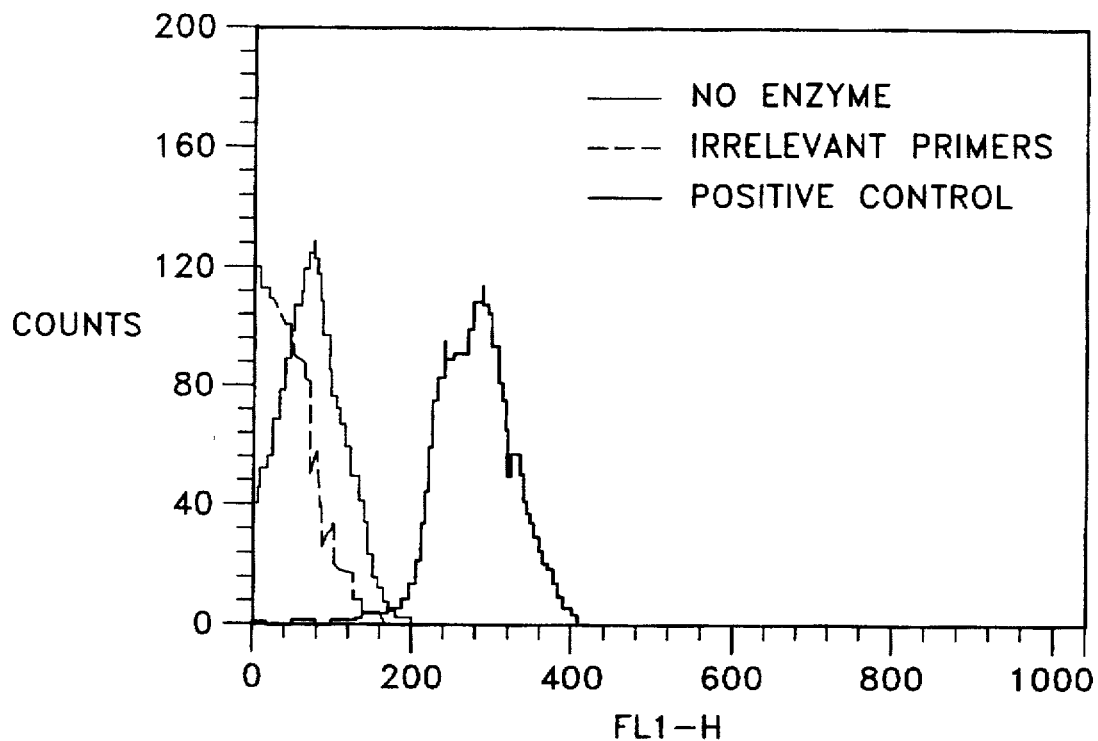
FIG-1B  HIV DNA AMPLIFICATION
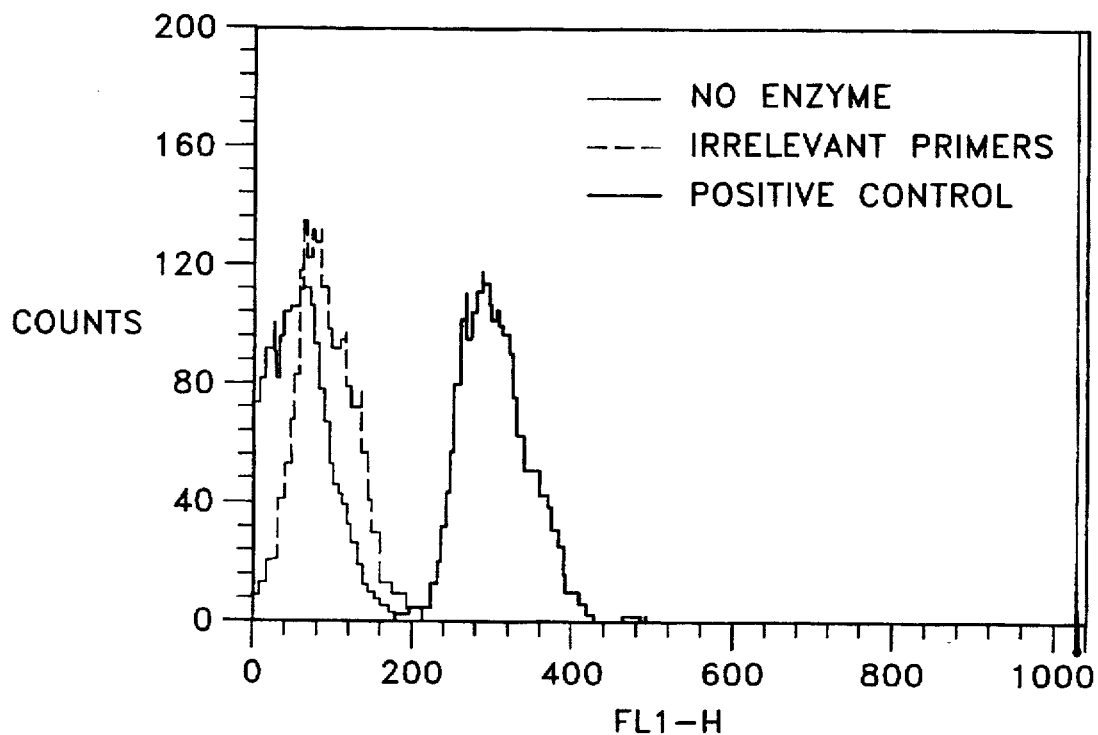

DETECTION OF NUCLEIC ACIDS IN CELLS BY THERMOPHILIC STRAND DISPLACEMENT AMPLIFICATION

This is a continuation of application Ser.No. 08/531,747, filed Sep. 21, 1995 U.S. Pat. No. 5,631,147.

FIELD OF THE INVENTION

The present invention relates to amplification of nucleic acids and in particular to amplification of nucleic acids in morphologically intact cells.

BACKGROUND OF THE INVENTION

Nucleic acid amplification techniques have provided powerful tools for detection and analysis of small amounts of nucleic acids. The extreme sensitivity of such methods has lead to attempts to develop them for early diagnosis of infectious and genetic diseases, isolation of genes for analysis, and detection of specific nucleic acids in forensic medicine. Nucleic acid amplification techniques can be grouped according to the temperature requirements of the procedure. The polymerase chain reaction (PCR), ligase chain reaction (LCR) and transcription-based amplification require repeated cycling of the reaction between high (85° C.–100° C.) and low (30° C.–40° C.) temperatures to regenerate single stranded target molecules for amplification. In contrast, methods such as Strand Displacement Amplification (SDA), self-sustained sequence replication (3SR) and the Qβ replicase system are isothermal reactions which can be performed at a constant temperature.

In the PCR, the temperature of the reaction is raised after primer extension to separate the newly-synthesized strand from the template. The temperature is then lowered to reanneal the primers and repeat the extension process. The steps of the PCR reaction therefore occur in discrete phases or cycles as a result of the temperature constraints of the reaction. In contrast, in Strand Displacement Amplification (SDA), extension of primers, displacement of single stranded extension products, annealing of primers to the extension products (or the original target sequence) and subsequent extension of the primers occur concurrently in the reaction mix. Conventional SDA (performed at lower temperatures, usually about 35°–45° C.) is described by G. T. Walker, et al. (1992a. *Proc. Natl. Acad. Sci. USA* 89, 392–396 and 1992b. *Nuc. Acids. Res.* 20, 1691–1696). A thermophilic version of the SDA reaction (tSDA, described below) has recently been developed, and is performed at a higher, but still constant, temperature using thermostable polymerases and restriction endonucleases.

Targets for amplification by SDA may be prepared by fragmenting larger nucleic acids using the endonuclease used in the SDA reaction. However, when the target is not flanked by the necessary restriction endonuclease recognition sites for fragmentation, target nucleic acids having appropriate restriction endonuclease recognition sites for nicking in the SDA reaction can be generated as described by Walker et al. (1992b. supra) and in U.S. Pat. No. 5,270,184. As in SDA, the individual steps of the target generation reaction occur concurrently and continuously, generating target sequences with the terminal recognition sequences required for nicking by the restriction enzyme in SDA. As all of the components of the SDA reaction are present in the target generation reaction, generated target sequences automatically and continuously enter the SDA cycle and are amplified.

In situ methods of nucleic acid analysis allow detection and localization of specific nucleic acid sequences within morphologically intact cells. These methods have conventionally been based on direct hybridization of labeled probes, for example as described in U.S. Pat. No. 4,888,278. However, such direct hybridization methods, while specific for the nucleic acid of interest, may not be sufficiently sensitive to detect very low copy numbers of the nucleic acid in all cases. As a means for detecting very low copy numbers, in situ amplification of the target sequence prior to in situ detection has been of great interest. In situ nucleic acid amplification methods have the potential to be more sensitive than conventional solution amplification because the cell may concentrate the amplification product, thereby allowing detection of fewer molecules than is possible when amplification products are free to diffuse or when they are diluted by the contents of cells which do not contain the sequence of interest. Because the nucleic acid need not be extracted from the cell prior to detection of the target sequence, in situs methods provide information as to which cells in a population contain a particular nucleic acid and further permit analysis of the nucleic acid in the context of the biochemical and morphological characteristics of the cell. In situ amplification methods have primarily been developed for the PCR (O. Basgara and R. Pomerantz. 1993. *AIDS Research and Human Retroviruses* 9(1), 69–76; G. Nuovo, et al. 1992. *Diag. Molec. Pathol.* 1(2), 98–102; M. J. Embleton, et al. 1992. *Nuc. Acids Res.* 20(15), 3831–3837; J. Emmetson, et al. 1993. *Proc. Natl. Acad. Sci. USA* 90, 357–361; P. Komminoth, et al. 1992. *Diag. Molec. Pathol.* 1(2), 85–97; K. P. Chile, et al. 1992. *J. Histochem. Cytochem.* 40(3), 333–341; Haase, et al. 1990. *Proc. Natl. Acad. Sci. USA* 87, 4971–4975; O. Basgara, et al. 1992. *New. Engl. J. Med.* 326(21), 1385–1391; Patterson, et al. 1993. *Science* 260, 976–979). However, the multiple cycles of heating and cooling, and stringent hybridization conditions required by the PCR to achieve its sensitivity are not well tolerated by tissues and cells. Diffusion of the amplified sequences out of the cells may be increased by the repeated heating, resulting in increased diffuse signal throughout the sample. To attempt to reduce the loss of PCR products from the cell, extensive fixation (15 hours to days) with cross-linking fixatives is often employed for in situ amplification by the PCR. This treatment often necessitates protease treatment of the fixed cells prior to amplification (G. Nuovo, et al. 1992. *Diag. Molec. Pathol.* 1(2), 98–102).

Conventional low temperature SDA, performed in situ, has been found to have many advantages over in situ PCR, including 1) improved maintenance of cell structure which allows immunophenotyping for cell identification, and 2) significantly improved retention of amplicons within the cell. It was uncertain, however, what effect the increased temperature of in situ tSDA would have on these features. While the increase in temperature (generally about 15°–20° C. as compared to conventional SDA) might provide the advantages of increased specificity and speed of the reaction, it could also significantly increase cell destruction, possibly to a level which would interfere or prevent accurate immunophenotyping and cell identification. The marked increase in reaction temperature could also increase diffusion of amplicons out of the cell where they could be taken up by negative cells and produce a false positive signal. It was unexpectedly found, however, that cell structure following in sites tSDA remained substantially intact as evidenced by normal forward and side light scatter properties on flow cytometry. Thus, immunophenotyping is compatible with the temperatures and protocols of in situ tSDA. Applicants hypothesize that maintaining the cells at the higher temperatures may be less damaging than subjecting them to repeated cycles of heating and cooling as in PCR. It was also unexpectedly discovered that diffusion of amplicons was not generally significantly increased, also possibly because the cells may sustain less damage when maintained at a constant high temperature than when subjected to thermocycling.

The following terms are defined herein as follows:

An amplification primer is a primer for amplification of a target sequence by hybridization and extension of the primer. For SDA, the 3' end of the amplification primer is a target binding sequence which hybridizes at the 3' end of the target sequence. The amplification primer further comprises a recognition site for a restriction endonuclease 5' to the target binding sequence, generally near its 5' end. The restriction endonuclease recognition site is a nucleotide sequence recognized by a restriction endonuclease which will nick a double stranded recognition site for the restriction endonuclease when the recognition site is hemimodified, as described by Walker, et al. (1992a), supra. A hemimodified recognition site is a double stranded recognition site for a restriction endonuclease in which one strand contains at least one derivatized nucleotide which prevents cutting of one of the strands of the duplex by the restriction endonuclease. "Nicking" refers to this modified activity, in which only one strand of the duplex is cut by the restriction endonuclease, in contrast to typical double-stranded cleavage. Any hemimodified restriction endonuclease recognition site which is nickable by a restriction endonuclease is suitable for use in SDA. Amplification primers for SDA are designated $S_1$ and $S_2$ by Walker, et al. (1992b), supra. Alpha-thio modified deoxyribonucleoside triphosphates are abbreviated "dNTPαS," "dATPαS," "dCTPαS," etc.

A "bumper" or external primer is a primer which anneals to a target sequence upstream of an amplification primer, such that extension of the external primer displaces the downstream primer and its extension product, i.e., a copy of the target sequence comprising the restriction endonuclease recognition site contributed by the amplification primer is displaced. The bumper primers therefore consist only of target binding sequences and are designed so that they anneal upstream of the amplification primers and displace them when extended. External primers are designated $B_1$ and $B_2$ by Walker, et al. (1992b), supra. Extension of external primers is one method for displacing the extension products of amplification primers, but heating may also be suitable in certain cases.

The terms target or target sequence refer to nucleic acid sequences (DNA and/or RNA) to be amplified. These include the original nucleic acid sequence to be amplified and its complementary second strand as well as either strand of a copy of the original target sequence produced by amplification of the target sequence.

Amplification products, extension products or amplicons are oligo or polynucleotides which comprise copies of the target sequence produced during amplification of the target sequence.

SUMMARY OF THE INVENTION

Thermophilic Strand Displacement Amplification (tSDA) has been adapted for amplification of nucleic acid target sequences in situ in cells in suspension, on slides or in tissues, with speed, sensitivity and specificity which is superior to conventional it, sill SDA. Excellent specimen morphology is preserved in spite of exposure to temperatures significantly higher than in conventional in situ SDA, as demonstrated by normal light scatter parameters on flow cytometry. In situ amplification by tSDA also remains compatible with immunochemical techniques in spite of the increased reaction temperature, so both amplification of target sequences and immunological staining can be performed on the same specimen. This is in contrast to the in situ PCR, in which the repeated temperature cycling may make the cellular antigens of interest undetectable by immunochemical techniques.

The inventive methods for in situ tSDA generally comprise a brief fixation of the cells or tissue, followed by permeabilization and addition of the reagents required for tSDA. When the target sequence is DNA the cells or tissues are heated briefly prior to amplification to denature the target sequence. Because of the thermostability of the enzymes involved, heating may optionally take place in a mixture of reagents which includes the enzymes. Alternatively, the enzymes may be added after denaturation, upon cooling the sample to the desired reaction temperature. The tSDA reaction is typically incubated at 50°–65° C. for 1 min. to 2 hr., although higher temperatures are possible if compatible with the selected enzymes. If no prior heating is required to denature the target sequence, all of the SDA reaction components are simply added directly to the fixed, permeabilized cells at the desired reaction temperature to initiate amplification. After washing to remove unused primers and enzymes, the amplification products are detected in situ or after release from the cells.

DESCRIPTION OF THE DRAWINGS

FIGS. 1A–1B shows the flow cytometric results for amplification of an HIV target sequence and an HLA-DQα exon 3 target sequence by in situ tSDA.

DETAILED DESCRIPTION OF THE INVENTION

The inventive methods for in situ nucleic acid amplification by tSDA are based on the discovery that tSDA in situ provides the significantly improved sensitivity, speed and specificity of in vitro (solution) tSDA protocols without significant loss of cellular structure and morphology. In general, a sample of cells (e.g., cells in suspension or tissue sections) suspected of containing nucleic acid target sequences is fixed with a fixative which maintains the morphological integrity of the cell but does not cross-link or precipitate cellular proteins so extensively that penetration of primers and other reagents is prevented. Treatment with protease after fixation to obtain penetration of primers and reagents into the fixed cells is therefore generally not required.

Either cross-linking or precipitating fixatives may be used in the practice of the invention. Examples include paraformaldehyde, 4% glutaraldehyde, ethanol/acetic acid fixatives, Carnoy's fixative (acetic acid, ethanol, chloroform), 1% osmium tetroxide, Bouin's fixative (1.21% picric acid, 11% formaldehyde, 5.6% acetic acid), Zenker's fixative (5.0% mercuric chloride, 2.5% potassium dichlorate, 5.0% acetic acid, 1.0% sodium sulfate), and acetic acid/inethanol fixatives. The use of FACS™ Lysing Solution allows lysis, fixation and permeabilization using a single reagent. The preferred fixative for use in the invention is 1–4% paraformaldehyde, which is preferably used to treat the cells or tissues for about 1 min. to 1 hr. It is generally useful to permeabilize the fixed cells prior to amplification, e.g., using detergents such as NP40, TRITON or saponin. Under certain circumstances, fixing may be optional. That is, tSDA may be performed in situ in unfixed cells, especially when RNA targets are to be selectively amplified and no preliminary heat denaturation step is required (see below).

It is an important feature of the present invention that either RNA or DNA target sequences, or both, may be amplified directly using the inventive methods. To amplify only RNA, a reverse transcriptase may be added to the tSDA reaction as it is in reverse transcription PCR (rtPCR—G. J. Nuovo, et al. 1992. *Diag. Molec. Pathol.* 1, 98–102; G. J. Nuovo, et al. 1991. *Am. J. Pathol.* 58, 518–523; G. J. Nuovo, et al. 1991 *Am. J. Pathol.* 139, 1239–1244). However, several of the DNA polymerases used in tSDA have now been found to exhibit reverse transcriptase activity. They can polymerize DNA copies of a target sequence using either RNA or DNA as the template, with incorporation of dNTPαS and displacement from a nick. RNA target sequences may therefore be reverse transcribed by the same polymerase which performs the DNA amplification portion of the tSDA reaction, without the need to add a separate reverse transcriptase. RNA may be amplified in the cells (i.e., without substantial amplification of DNA targets) by eliminating the heat denaturation step or treating with DNase prior to initiating the tSDA reaction. The double stranded DNA in the cells then remains double stranded and unavailable as a template, whereas primers can hybridize to available single stranded RNA and begin specific amplification of RNA target sequences by generating cDNA. The cDNA in turn serves as a template for further amplification. Specific amplification of RNA target sequences may also be accomplished by treating the cells with RNase-free DNase prior to initiating SDA. As fixation aids in maintaining the integrity of the cells during heating, fixing may not be needed when there is no preliminary heat denaturation step. It may still be useful, however, to permeabilize the unfixed cells or tissues Treatment of the cells or tissues with RNase prior to heat denaturation of double stranded DNA degrades potential RNA target sequences and allows specific amplification of the corresponding DNA target sequences. NaOH (about 0.1M) may also be used to selectively degrade RNA and denature DNA for DNA-specific amplification.

If the heat denaturation step is included (without RNase treatment) prior to annealing of the SDA primers, both DNA and RNA target sequences will be amplified. In situ reverse transcription of RNA by the DNA polymerases used in tSDA is generally less efficient than DNA synthesis, but has unexpectedly been found in some cases to be more efficient than conventional reverse transcriptases. However, RNA targets are usually present in the cell in greater numbers than the corresponding DNA target, and the high efficiency of amplification of the cDNAs which are generated quickly overcomes and compensates for any reduced efficiency in the reverse transcription step of the reaction. Amplification of both RNA and DNA targets is preferred for most diagnostic applications of the invention because this gives the greatest number of amplifiable target sequences per cell and, as a result, the greatest sensitivity and largest number of potentially positive cells per sample.

If the target is to be heat denatured prior to amplification, the fixed cells or tissues may be heated in the SDA reaction mixture (e.g., dNTPs, KiPO$_4$, MgCl$_2$, BSA, DMSO, external primers, amplification primers, and enzymes if they are sufficiently heat-stable). If the polymerase and restriction endonuclease are not sufficiently heat stable at the temperature of denaturation, they may be added subsequently when the sample has been cooled to the desired reaction temperature. If the target is not heat denatured, the SDA reaction mixture including the restriction endonuclease and polymerase(s) may simply be added to the cell sample at the selected reaction temperature to initiate amplification.

As for conventional SDA, targets for amplification by tSDA may be prepared by fragmenting larger nucleic acids by restriction with an endonuclease which does not cut the target sequence. However, for both in situ tSDA and in situ conventional SDA it is generally preferred that target nucleic acids having the selected restriction endonuclease recognition/cleavage sites for nicking in the amplification reaction be generated as described by Walker, et al. (1992, *Nuc. Acids. Res., supra*) and in U.S. Pat. No. 5,270,184.

To prevent cross-contamination of one SDA reaction by the amplification products of another, dTTP may be incorporated into SDA amplicons in place of dTTP without significant inhibition of the amplification reaction. The uracil-containing nucleic acids may then be specifically recognized and inactivated by treatment with UDG (uracil DNA glycosylase). Therefore, if dUTP is incorporated into SDA amplicons in a prior reaction, any subsequent SDA reactions can be treated with UDG prior to amplification of double stranded targets, and any dU containing DNA from previously amplified reactions will be rendered unamplifiable. The target DNA to be amplified in the subsequent reaction does not contain dU and will not be affected by the UDG treatment. UDG may then be inhibited by treatment with Ugi (uracil DNA glycosylase inhibitor) prior to amplification of the target. Alternatively, UDG may be heat-inactivated. In tSDA, the higher temperature of the reaction itself ($\geq 50°$ C.) can be used to concurrently inactivate UDG and amplify the target.

SDA requires a polymerase which lacks 5'→3' exonuclease activity, initiates polymerization at a single stranded nick in double stranded nucleic acids, and displaces the strand downstream of the nick while generating a new complementary strand using the unnicked strand as a template. Polymerase displacement activity is essential to the amplification reaction, as it makes the target available for synthesis of additional copies and generates the single stranded extension product to which a second amplification primer may hybridize in exponential amplification reactions. More processive polymerases are preferred, as they may maximize the length of target sequence which can be amplified.

Little was previously known about the activities of thermophilic polymerases at temperatures which would be appropriate for tSDA. Further, the activities of thermophilic polymerases at temperatures compatible with activity for thermophilic restriction endonucleases was not known. Screening assays were therefore developed to identify candidate restriction endonucleases and polymerases. if any existed. The polymerase screening system is an extension assay which tests the ability of the polymerase to displace a downstream strand initiating at a single stranded nick in a double stranded template. It also tests for the presence or absence of 5'→3' exonuclease activity. 5'→3' exonuclease activity, if present in an otherwise suitable thermophilic polymerase, can be inactivated by routine methods known in the art (WO 92/06200). One of the most common methods for selectively inactivating exonuclease activity in a polymerase is to clone the gene for the polymerase, identify the portion of the gene sequence which encodes the protein domain responsible for exonuclease activity, and inactivate it by in vitro mutagenesis. Alternatively, exonuclease activity may be inactivated by treating the polymerase with protease to isolate fragments which exhibit only the desired polymerization and displacing activities. Therefore, a thermophilic polymerase identified in the extension assay which is active at a suitable temperature, initiates extension at a nick and incorporates modified dNTPs but has 5'→3' exonuclease activity can be made suitable for tSDA by elimination of the exonuclease activity.

In the extension assay for polymerases, displacement of the single strand from a double stranded nucleic acid and initiation at a nick is staged by annealing two primers immediately adjacent to each other on an intact sequence complementary to both primers. The primers are labeled at their 5' ends, usually with $^{32}$P. If a polymerase has strand displacement activity, is able to initiate polymerization at the "nick" formed by the adjacent hybridized primers and lacks 5'→3' exonuclease activity, both primers are extended and two extension products will be detected. If the polymerase lacks 5'→3' exonuclease activity but cannot initiate extension at the nick (e.g., it requires a gap) and/or if it lacks displacement activity, only the extension product of the downstream primer will be detected. A polymerase which initiates at a nick but has 5'→3' exonuclease activity will generate only the extension product of the upstream primer. The extension assay also requires that the polymerase be capable of incorporating an α-thio dNTP (dNTPαS), which is included in the reaction. Upstream and downstream primers and their respective extension products are generally identified by size on gels with autoradiography.

Of eleven thermophilic DNA polymerases initially screened in the extension assay, six were identified as having all of the required characteristics for use in the invention: exo⁻ Vent (New England Biolabs), exo⁻ Deep Vent (New England Biolabs), Bst (BioRad), exo⁻ Pfu (Stratagene), Bca (Panvera), and Sequencing Grade Taq (Promega). Others may be routinely identified using the foregoing extension assay without the exercise of inventive skill, and all such polymerases would be suitable for use in tSDA. The polymerases Tth (Boehringer), Tfl (Epicentre), REPLINASE (DuPont) and REPLITHERiM (Epicentre) strand displace from a nick, but also have 5'→3' exonuclease activity. These polymerases are useful in the methods of the invention after removal of the exonuclease activity, e.g., by genetic engineering. Most of the thenioplilic polymerases identified to date are active between about 50° C. and 75° C. with optimal activity at about 65° C.–75° C. and reduced activity at about 50° C.–65° C. However, as the thermostability of thermophilic restriction endonucleases is generally limited to less than 65° C., thermophilic polymerases with optimal activity at lower temperatures (e.g., Bst and Bca) are more compatible with thermophilic restriction endonucleases in the reaction and are therefore preferred. However, restriction endonucleases which are active at higher temperatures compatible with the usual optimum temperatures for polymerase activity may be identified and are also useful in the invention.

Restriction endonucleases suitable for SDA must cleave only one of the strands of a double stranded hemimodified recognition/cleavage site for the restriction endonuclease ("nicking"). This nicking activity is of great importance, as it is nicking which perpetuates the reaction and allows subsequent rounds of target amplification to initiate. Because restriction enzymes generally produce double strand breaks, cleavage of one of the two strands in the duplex cleavage site must be selectively inhibited. This is usually accomplished by introducing nucleotide analogs (e.g., deoxynucleoside phosphorothioates) into one strand of the DNA during synthesis so that either the modified strand or the unmodified strand is no longer susceptible to cleavage. In cases where the unmodified strand is protected from cleavage, nucleotide analogs may be incorporated into the primer during its synthesis, thus eliminating both the need to add nucleotide analogs to the amplification reaction and the requirement that the polymerase be capable of incorporating such nucleotide analogs.

As nucleotide analog substitutions do not induce nicking by all restriction endonucleases, a means for assaying the nicking characteristics of restriction endonucleases was required in order to identify suitable enzymes which might exist among the many available thermophilic restriction endonucleases. Therefore, a screening system for identifying thermophilic restriction endonucleases with the desired properties was devised based on the ability of a modified deoxynucleotide incorporated into one strand of the double stranded restriction endonuclease recognition/cleavage site to protect one of the two strands from cleavage by the endonuclease. This is referred to as the analog-induced nicking assay or the strand protection assay.

In the strand protection assay, a single stranded template comprising the restriction endonuclease recognition/cleavage site and a primer complementary to a portion of the template other than the recognition/cleavage site are synthesized. The template and the primer are then labeled, typically with a radiolabel. The primer and template are hybridized and modified dNTPs are incorporated by extension of the primer, producing a fully double stranded molecule containing a hemimodified restriction endonuclease recognition/cleavage site. This product is treated with the restriction endonuclease under conditions appropriate for double-stranded cleavage. Electrophoretic analysis of the reaction products under denaturing conditions is used to determine, by the size of the fragments generated, whether or not the recognition/cleavage site was nicked, cleaved or uncut. The size of the fragments on electrophoresis is also used to determine which of the two strands of the recognition/cleavage site (i.e., modified or unmodified) was protected from cleavage. The strand protection assay may be routinely adapted to screen additional restriction endonucleases for utility in the invention, without the exercise of inventive skill.

Using the strand protection assay, twenty-eight thermophilic restriction endonucleases were tested (AccI, AspI, BsaI, BsaBI, BsiYI, BslI, two degenerate sites of BsmI, BsmAI, BsmFI, BsmHI, BspWI, four degenerate sites of BsoBI, BsoFI, two degenerate sites of BsrI, BsrBRI, two degenerate sites of BsrDI, Bst7II, two degenerate sites of BstNI, BstOI, BstXI, DpnI, HaeII, MamI, MboI, MvaI, MwoI, SfiI, and TthllII). Of the twenty-eight, eleven had at least one restriction endonuclease recognition/cleavage site which was nicked upon introduction of at least one α-thio dNTP: AccI, BslI, BsmI, BsmAI, BsoBI, BsrI, BsrDI, BstNI, BstOI, BstXI, and MwoI. One of the recognition sites of BsmI exhibited protection of the unmodified strand when dCTPαS was incorporated. When tested for thermostability at 50°–65° C., all but one of the eleven (AccI) were sufficiently stable or could be sufficiently stabilized by addition of common stabilizers such as double-stranded DNA or BSA. These endonucleases were therefore compatible with the thermophilic polymerases in the tSDA reaction.

In addition, several thermophilic endonucleases were identified which had partial or low nicking activity under the initial screening conditions of the strand protection assay (e.g., TthlllI, BsiYI and BsoFI). While reduced nicking activity would not prevent SDA, nicking by a restriction endonuclease may be optimized by adjusting the the reaction conditions (e.g., by optimizing the buffer or adjusting the reaction temperature), making them more efficient in tSDA. In addition, as it is known that sequences flanking a restriction endonuclease recognition/cleavage site may affect the degree of endonuclease activity, altering the flanking sequences of the templates may also improve nicking activity for endonucleases which nicked only partially.

Thermophilic SDA is performed essentially as conventional SDA, with substitution of the desired thermostable polymerase and thermostable restriction endonuclease. Of course, the temperature of the reaction will be adjusted to the higher temperature suitable for the selected thermophilic enzymes and the conventional restriction endonuclease recognition/cleavage site will be replaced by the appropriate restriction endonuclease recognition/cleavage site for the selected thermostable endonuclease. Also in contrast to conventional SDA, the practitioner may include the enzymes in the reaction mixture prior to the initial heat denaturation step if they are sufficiently stable at that temperature. Preferred restriction endonucleases for use in tSDA are BsrI, BstNI, BsmAI, BslI and BsoBI (New England BioLabs), and BstOl (Promega). The preferred thermophilic polymerases are Bca and Bst.

To develop an optimized SDA system capable of high amplification factors (e.g., $10^8$–$10^9$), evaluation and optimization of the buffer systems is recommended. This is also the case when evaluating a new restriction enzyme/polymerase pairing for use in thermophilic SDA. Such optimization methods may be applied to determine an appropriate buffer for any restriction endonuclease/polymerase combination for tSDA, requiring only routine testing without the exercise of inventive skill. In most cases the KPO4 /MgCl$_2$ buffer typically employed in conventional SDA is suitable for tSDA, either as described or with some routine modification of the concentrations of the components.

In in sitU tSDA, the reagents for amplification are applied to unfixed cells or cells which have been fixed and permeabilized as described above. After initiation of the reaction, amplification of the target sequence is generally allowed to proceed at about 50°–65° C. for about 1 min to 2 hr., preferably about 10 min. to 1 hr. It has been discovered that the time required for in situ amplification by tSDA or conventional SDA is significantly less than the time required to obtain a comparable level of target amplification in situ by the PCR. In certain cases it may be advantageous to increase the concentration of reagents (especially primers) for in situ tSDA as compared to in vitro tSDA to ensure that sufficient amounts enter the cells for efficient amplification. Leakage of amplicons from the cells has been a problem in certain in situ nucleic acid amplification methods. Such leakage is believed to be the result of the complex interaction of a variety of parameters, e.g., size of the amplicon, temperature, temperature cycling and the degree to which the cell has been permeabilized. To facilitate retention of amplicons within the cell, a deoxyribonucleoside triphosphate (dNTP) analog comprising the dNTP conjugated to a moiety such as digoxigenin ("dig"), biotin or fluorescein isothiocyanate (FITC) may optionally be incorporated into the amplification products along with the dNTPαS. The additional dNTP analog may also, optionally, serve as a tag or label to be used for detecting amplification products. Incorporation of dNTP analogs such as dig also has the advantage of providing an enhanced signal, as each incorporated label moiety can generate a signal by binding to anti-dig antibodies conjugated to alkaline phosphatase (AP-α-dig). Incorporation of such dNTP analogs is particularly advantageous for in situ SDA because the amplified target sequence is generally smaller than a PCR amplicon. It has been observed, however, that even though SDA amplicons are generally smaller than PCR amplicons, there is less leakage associated with in situ conventional SDA than with in situ PCR. Because of the higher temperature of in situ tSDA, it was anticipated that amplicon leakage might be increased, possibly to the level observed in in situ PCR. In practice, however, although there may be a slight increase in amplicon leakage at the elevated temperatures, there is still significantly less amplicon leakage in in situ tSDA than there is in in situ PCR.

Following target amplification, the amplicons produced may be detected by any of the methods known in the art for detection of specific nucleic acid sequences. For example, amplification products may be detected in situ or after release of amplicons from the cells by specific hybridization to an oligonucleotide detector probe. The detector probe is a short oligonucleotide which includes a detectable label, i.e., a moiety which generates or can be made to generate a detectable signal. The label may be incorporated into the oligonucleotide probe by nick translation, end-labeling or during chemical synthesis of the probe. Many directly and indirectly detectable labels are known in the art for use with oligonucleotide probes. Directly detectable labels include those labels which do not require further reaction to be made detectable, e.g., radioisotopes, fluorescent moieties and dyes. Fluorescent labels such as fluorescein isothiocyanate (FITC) or radioisotopes such as $^{32}$p are preferred for use in labeling probes for direct detection of target sequences amplified in situ. Indirectly detectable labels include those labels which must be reacted with additional reagents to be made detectable, e.g., enzymes capable of producing a colored reaction product, biotin, avidin, digoxigenin, antigens, haptens or fluorochromes. The signal from enzyme labels is generally developed by reacting the enzyme with its substrate and any additional reagents required to generate a colored enzymatic reaction product. Biotin (or avidin) labels may be detected by binding to labeled avidin (or labeled biotin) or labeled anti-biotin (or labeled anti-avidin) antibodies. Digoxigenin and hapten labels are usually detected by specific binding to a labeled anti-digoxigenin (anti-dig) or anti-hapten antibody. Enzymes are preferred for use as indirectly detectable labels in the present invention. Most preferred is alkaline phosphatase (AP) because it is stable and has been used extensively for labeling in tissues and cells. The presence of AP may be detected by reaction with a substrate. The preferred substrates for detection of AP are Vector Red/Vector Blue (Vector Labs, CA), 5-bromo-4-chloro-3-indolyl phosphate (BCIP)/nitro blue tetrazolium (NBT) (Sigma Chemical Company, St. Louis, Mo.) or Nuclear Fast Red (Sigma Chemical Company). Vector Red has the added advantage of fluorescence, allowing visualization of a positive signal either by conventional light microscopy or by fluorescence microscopy. Methods for developing the colored reaction product of AP with these substrates are known in the art.

To detect amplified target sequences by hybridization to a detector probe, the cells or tissues are exposed to the labeled probe under reaction conditions appropriate for specific hybridization of the probe to single stranded amplification products. In general, the detector probe will be selected such that it hybridizes to a nucleotide sequence in the amplicon which is between the binding sites of the two amplification primers. However, a detector probe may also have the same nucleotide sequence as either of the amplification primers. Suitable methods for detection by in situ hybridization to a detector probe are described by J. B. Lawrence et al. (1989. Cell 57, 493–502), J. B. Lawrence, et al. (1990. Proc. Natl. Acad. Sci. USA 87, 5420–5424) and in U.S. Pat. No. 4,888,278.

Alternatively, amplification products may be detected in situ or after release from the cells by primer extension as described by Walker, et al. (1992b), supra. In the primer extension method an oligonucleotide primer comprising a detectable label is hybridized to the amplification products and extended by addition of polymerase. For detection the primer may be 5' end-labeled, preferably using $^{32}P$ or a fluorescent label. Alternatively, extension of the hybridized primer may incorporate a dNTP analog comprising a directly or indirectly detectable label. For example, extension of the primer may incorporate a dig-derivatized dNTP, which is then detected after extension by reaction with AP-α-dig and a suitable AP substrate. The primer to be extended may either be the same as an amplification primer or it may be a different primer which hybridizes to a nucleotide sequence in the amplicon which is between the binding sites of the amplification primers.

The detectable label may also be incorporated directly into amplicons during target sequence amplification. For example, one of the dNTPs in the conventional SDA reaction may be completely or partially replaced with a dNTP analog which comprises a dNTP conjugated to a directly or indirectly detectable label. For example, dUTP conjugated to the desired label may be substituted for dTTP in the SDA reaction. The polymerase then incorporates the label directly into the amplification products generated by extension of the amplification primer. The label may be directly or indirectly detectable. Preferably, the label conjugated to the dNTP is a fluorescent label which may be detected directly in the amplicons by fluorescence microscopy or flow cytometry. In an alternative preferred embodiment, the label conjugated to the dNTP is biotin or digoxigenin, which may be detected by reaction with streptavidin/FITC and fluorescence microscopy or flow cytometry.

Secondary amplification products are copies of the target sequence generated by hybridization and extension of a signal primer on the target sequence. The secondary amplification products comprise an internal segment of the amplified target sequence and a detectable label which is associated with the signal primer. At least the 3' end of the signal primer comprises a sequence which hybridizes to the target sequence. It may also include features which facilitate capture or immobilization of the secondary amplification products, so that they may be isolated for detection, quantitation or further manipulation. Concurrent generation of secondary amplification products in the in situ tSDA reaction provides another detection method which is homogeneous and may be performed concurrently with amplification. The lengthy in situ probe hybridization step is eliminated and concentrations of signal primer are lower than for hybridization probes. The lower concentration itself reduces background and also allows higher stringency washing which further reduces background. To generate secondary amplification products, at least one signal primer is included in the iii silll tSDA reaction mixture. The signal primer(s) hybridizes to the target sequence downstream of the hybridization site of an amplification primer and is extended by polymerase in a manner similar to extension of the amplification primer. Extension of the amplification primer displaces the downstream extension product of the signal primer from the target sequence. The opposite amplification primer can then hybridize to the extended, displaced signal primer and itself be extended by polymerase, resulting in incorporation of the signal primer into a longer duplex indicative of target amplification. As any remaining unextended signal primers are small, they can be washed out of the cell while the extended signal primers are retained within it. Target amplification-specific signal thereby becomes associated with the cells where the target is present and is substantially absent from cells where there is no target.

The label of the hybridized detector probe, extended primer, amplicon or secondary amplification product is then detected, preferably in situ as an indication of the presence of amplified target sequences. This may require the addition of reagents to the cells to develop the signal of an indirectly detectable label such as AP, biotin or dig. Microscopic analysis of the cells is preferred when the detectable label is an enzyme. Microscopic analysis may be either by visual observation of the cells or tissues (fluorescence or light microscopy), or automated image analysis using instruments such as DISCOVERY (Becton Dickinson Image Cytometry, Leiden, Holland) to evaluate the number and signal intensity of positive cells. When the label is a radiolabel, the cells may be suspended in scintillation fluid and the signal detected by scintillation counting. Use of a directly detectable fluorescent label allows fluorescence analysis of cells in suspension by flow cytometry (e.g., FACSCAN, Becton Dickinson Immunocytometry Systems, San Jose, Calif.). A shift in peak fluorescence to the right on a plot of cell number vs. fluorescence intensity is indicative of an increased number of cells containing the target sequence. Conversely, a shift in peak fluorescence to the left on the plot is indicative of a reduced number of cells containing the target sequence. Alternatively, amplification products may be released from cells prior to detection as described above or visualized after gel electrophoresis as bands of amplification products, e.g., by EtBr staining, hybridization of a detector probe or primer extension. When a radiolabel is used for the primer or detector probe, amplification products may be visualized by autoradiography of the gels.

Conventional methods of preparing cells for in situ amplification and analysis by flow cytometry involve isolation of peripheral blood mononuclear cells from whole blood (PBMCs—e.g., by FICOLL gradient centrifugation) prior to antibody staining and/or amplification. An additional step to isolate T cells fromthe PBMCs may also be necessary. Such conventional protocols require approximately two days to obtain flow cytometric results for a whole blood sample. It has now been discovered that a whole blood sample can be fixed and amplified in situ with flow cytometric analysis in a single day using FACS™ Lysing Solution (Becton Dickinson Immunocytometry Systems, San Jose, Calif.) to prepare the sample. This lysing reagent comprises diethylene glycol, heparin, citrate buffer and formaldehyde, pH 7.2. Because of the presence of formaldehyde, FACS™ Lysing Solution provides the advantage of reducing the biohazard from biological samples. In the new sample preparation protocol, the sample is simply lysed with FACS™ Lysing Solution, then fixed, permeabilized, and amplified in situ as described above. When cells in suspension or in tissues are to be analyzed both by in situ tSDA and immunostaining, it is preferred that the antibody be bound to the epitope or antigen of interest prior to lysis and fixation, and that the antibody be conjugated to an indirectly detectable label, e.g., biotin. The antibody-conjugate is then stabilized on the cells by fixation. After in situ tSDA, the bound antibody is detected by reaction with appropriate signal developing reagents, e.g., streptavidin conjugated to a fluorochrome or anti-biotin conjugated to a fluorochrome. The fluorochrome for detection of target amplification and the fluorochrome of the antibody may be separately detectable on flow cytometry, allowing the practitioner to simultaneously determine the presence of target in a cell and identify the type of cell in which the target is found. The new sample preparation protocol may be further shortened by inclusion of a fluorescently labeled signal primer in the amplification reaction. As described above, the signal primer is extended and rendered double stranded during the amplification reaction in a target amplification-specific manner, eliminating the need for additional post-amplification steps to detect amplification products.

Design of amplification primers for SDA generally requires synthesis of multiple primers directed to the target region of interest, followed by testing of pairwise combinations of primers in SDA reactions to determine the amplification efficiency of each pair. This is because the parameters which affect SDA primer performance are not well understood. We have found that apparently insignificant changes in the target binding regions of amplification primers for SDA can have a significant and unpredictable effect on amplification efficiency and that the melting point of the target binding region is not necessarily related to priming efficiency. In the development of in situ tSDA, a first pair of amplification primers was designed which was specific for the gag gene of HIV. A target region of the gag gene which did not contain a recognition site for the SDA restriction endonuclease was selected. The target region was also selected on the basis of having two regions of approximately 50 bp each which were approximately 100 bp apart and relatively invariant. Primer design software was then used to determine the melting point of the target binding of each primer candidate and to assess the potential for formation of primer dimers. Primers were modified or discarded accordingly to these preliminary results. A final list of eight candidate "left-side" amplification primers (directed to the 3' end of the target on the first strand) and nine candidate "right-side" amplification primers (directed to the 3' end of the target on the second strand) was compiled for experimental testing. Bumper primers and detector probes were designed taking into account only the melting point and suitable placement with respect to the amplification primers.

The amplification efficiency of pairwise combinations of "left-side" and "right-side" primers was determined experimentally in in vitro tSDA using a plasmid clone of the gag target, Bca polymerase and BsoBI. Amplicons were detected and quantified by hybridization and extension of a $^{32}$P labeled detector probe, followed by gel electrophoresis. The amplification primer pair with the best amplification efficiency in vitro was selected for further development in in situ. In a buffer system optimized as described above, this primer set detected less than ten copies of the gag target sequence in vitro tSDA (BsoBI sites are italicized, target binding sequences are underlined):

Left-Side Amplification Primer (SEQ ID NO: 1)
ACCGCATCGAATGCATGTCTCGGGTGG-TAAAAGTAGTAGAAG $T_M 41°$ C.

Right Side Amplification Primer (SEQ ID NO:2)
CGATTCCGCTCCAGACTTCTC-GGGGTGTTTAGCATGGTGTT $T_M$ 55° C.

Bumper Primers
AAATGGTACATCAGGCC $T_M 57°$ C. (SEQ ID NO:3)
GCAGCTTCCTCATTGAT $T_M 58°$ C. (SEQ ID NO:4)

Detector Probe (SEQ ID NO:5)
GGTGGCTCCTTCTGATAATG $T_M 63°$ C.

A pair of amplification primers specific for exon 3 of the HLA-DQα gene was designed in a similar manner, using human placental DNA for evaluation of the candidate amplification primer pairs in vitro. As the HLA genes are present in all cells, this target was to be used as a positive control for in situ tSDA. Because leakage of the amplicons was found not to be a significant problem, slightly smaller target regions were selected for the initial identification of candidate primers (about 75–100 bp). Three "left-side" amplification primers and three "right-side" amplification primers were initially designed and tested experimentally in pairwise combinations. In a buffer system optimized as described above, the following primer set gave the best amplification results, detecting less than five copies of the HLA-DQα exon 3 target sequence in in vitro tSDA:

Left-Side Amplification Primer (SEQ ID NO:6)
ACCGCATCGAATGCATGTCTCGGGTGGT-CAACATCACATGGC $T_M 60°$ C.

Right-Side Amplification Primer (SEQ ID NO:7)
CGATTCCGCTCCAGACTTCTCGGGT-GAGAGGAAGCTGGTC $T_M 53°$ C.

Bumper Primers
GTCTTGTGGACAACATCTTTCC $T_M 64°$ C. (SEQ ID NO:8)
TAACTGATCTTGAAGAAGGAATGATC $T_M 59°$ C. (SEQ ID NO:9)

Dectector Probe (SEQ ID NO:10)
AATGGGCACTCAGTCACAGA $T_M 65°$ C.

The target binding sequence confers target specificity on the amplification primer. The target binding sequences of the amplification primers of the invention are therefore also useful in nucleic acid amplification protocols other than SDA, e.g., PCR and 3SR. Specifically, any amplification protocol which utilizes cyclic, specific hybridization of primers to the target sequence, extension of the primers using the target sequence as a template and displacement of the extension products from the target sequence may employ the target binding sequences of the amplification primers of the invention. For amplification methods which do not require any specialized, non-target binding sequence, such as the restriction endonuclease recognition site of the amplification primers shown in the attached SEQUENCE LISTING (e.g., PCR), the amplification primers may consist of the target binding sequences only. Amplification methods which require different specialized, non-target binding sequences than those shown in the SEQUENCE LISTING (e.g., 3SR) may employ amplification primers comprising the target binding sequences of the amplification primers listed and the sequence or structure required by the selected amplification method as is known in the art. In addition, a different restriction endonuclease recognition site appropriate for tSDA may also be substituted for the restriction endonuclease recognition site shown in the SEQUENCE LISTING, using methods known in the art.

The following experimental examples are provided to illustrate certain embodiments of the invention, but are not to be construed as limiting the invention as defined by the appended claims.

EXAMPLE 1

The HLA-DQα exon 3 target was amplified and detected in situ in human acute myelogenous leukemia (AML) cells (KG-1a) using the selected primer set described above. The cells were first fixed for 30 min. in 4% paraformaldehyde and washed three times in 1X phosphate buffered saline (PBS). They were then permeabilized with 0.01% saponin for 20 min. and washed three times with 1X PBS. Five microliters of fixed, permeabilized cells ($10^8$ cells/ml in 35 mM KP$_i$, pH 7.6) were added to 40 μL of 35 mM KP$_i$, pH 7.6, 3 mM MgCl$_2$, 50 μM each dGTP, TTP and dATP, 1.4 mM dCTPαS, 500 nM amplification primers, 50 nM bumper primers and 15% glycerol. After gentle mixing, the samples were incubated at 95° C. for 2 min. and transferred to a THERMAL-LOK™ temperature block maintained at the reaction temperature (52° C.). Five microliters of the enzyme cocktail were then added (0.5 µL 10 NEB 2, 0.36 µL of 22 unit/ml Bca, 1.0 µL of 160 unit/ml BsoBI and 3.14 µL water) and mixed to start the amplification reaction. Final reaction volume was 50 µL. After 30 min., the reaction was stopped by placing on ice and amplification products were detected.

Radiolabeled detector probes (2×10⁶ cpm) were added to the amplification reaction and hybridized to the amplification products in situ for 3 min. at 95° C., followed by 60 min. at 37° C. After washing twice for 25 min. in 200 µL of 1X SSC, the cells were counted in scintillation fluid. The results of one such experiment were as follows:

| TUBE | IN SITU HYBRIDIZATION SIGNAL (cpm) | |
|---|---|---|
| 1 | 9510 | in situ tSDA, specific detector probe |
| 2 | 556 | negative control, specific detector probe |
| 3 | 828 | in situ tSDA, unrelated detector probe |
| 4 | 769 | negative control, unrelated detector probe |

In Tube 1, amplified KGla cells were probed with the HLA-DQα exon 3-specific detector probe. Tube 2 was a negative control in which the restriction endonuclease was omitted from the amplification reaction, preventing tSDA. Tubes 3 and 4 corresponded to Tubes 1 and 2, but were probed with the gag-specific detector probe, which is unrelated to the target sequence. All samples which were amplified in the presence of all necessary enzymes and were detected with the HLA-DQαexon 3-specific probe showed specific amplification of the intended target in situ.

The experiment was repeated to include incubation of unamplified cells with amplicons generated in situ. This was to evaluate the transfer of amplicons to negative cells, either by sticking of amplicons to the cell surface or uptake of the amplicons by negative cells. Following in situ amplification, the reaction was centrifuged to sediment the cells. The supernatant was incubated for 15 min. at 70° C. to eliminate BsoBI activity and added to fixed, penneabilized KGla cells which had previously been heated to 95° C. for 2 min. The mixture was incubated at 52° C. for 30 min. and the cells were then hybridized, washed and counted as above with both specific and non-specific (unrelated) detector probes. The results are shown below:

| TUBE | IN SITU HYBRIDIZATION SIGNAL (cpm) | |
|---|---|---|
| 1 | 2924 | negative control, specific detector probe |
| 2 | 16284 | in situ tSDA, specific detector probe |
| 3 | 17548 | 3× polymerase, specific probe |
| 4 | 5582 | cell incubation, specific probe |
| 5 | 871 | negative control, unrelated probe |
| 6 | 311 | in situ tSDA, unrelated probe |
| 7 | 501 | 3× polymerase, unrelated probe |
| 8 | 453 | cell incubation, unrelated probe |

Restriction endonuclease was omitted from the negative control reaction in Tube 1. Tubes 2 and 3 represented the complete amplification reaction with specific detection. Tube 3 shows the signal resulting from in situ tSDA under the same conditions as in Tube 2 but with a three-fold increase in polymerase concentration. In Tube 4, tSDA amplicons generated in situ were incubated with unamplified cells, which were then hybridized, washed and detected as in the amplified samples. Tube 4 was included to determine how much of the positive signal in Tube 2 due to non-specific sticking of amplicons to unamplified cells. Tubes 5–8 correspond to the reaction conditions of Tubes 1–4, except that the unrelated gag detector probe was hybridized as a negative control. As in the previous experiment, specific in situ amplification of the target clearly occurred in those samples which contained all necessary enzymes and were detected with the specific HLA-DQα exon 3 probe. False positive signal generation caused by a mechanism in which amplicons which may be found in the supernatant are taken up by unamplified cells may occur to some extent, but the substantially higher signal in tubes 2 and 3 clearly shows that in situ SDA is taking place. The majority of signal is target-specific and not due to amplicon transfer.

In an alternative detection system, the experiments were repeated using signal primers labeled with fluorescein. Signal primers were added to the amplification reaction at a concentration of 100 nM. The fluorescent probe was thereby extended by polymerase and displaced from the target by extension of the upstream amplification primer. After stopping the amplification reaction on ice, the samples were washed twice with 150–200 µl of phosphate buffered saline for five minutes each wash. Washing removed smaller, unextended signal priemrs from the cells, while the longer target amplification-specific fluorescent signal primers were retained by those cells in which amplification had occurred. In these experiments, the washed cells were visualized by fluorescence microscopy, where a strong fluorescent signal was observed in positive cells and negative cells were non-fluorescent.. However, signal primer extension is also compatible with detection and/or counting of fluorescent cells by flow cytometry.

In a third series of similar experiments, the amplification products were detected in a colorimetric assay. Cells were fixed in 4% paraformaldehyde for 20 min., washed three times in 1×PBS and permeabilized in 0.01% saponin for 10 min. After washing in SDA buffer (35 mM KPO₄pH 7.5, 15% glycerol, 4 mM MgOAc), 5 µL of the cell suspension (5×10⁵ cells) were added to 40 µL of SDA buffer with primers and dNTPs as above. The target was amplified using the HLA-DQα exon 3 primer set as before, adding 5 µL of the enzyme mixture after target denaturation, to make a final reaction volume of 50 µL. . The mouse cells served as a negative cell line because, in spite of the homology between human HLA and mouse MHC, the mouse MHC target is not amplified in this amplification system. Analysis of gene sequence databases revealed that homology between mouse and human in the binding regions of the primers used here is poor, and negativity was confirmed by failure to amplify purified mouse DNA in PCR using these primers. After denaturing for 2 min. at 94° C., digoxigenin-labeled detector probes (1–10 nM) were hybridized for 2 hr. at 33° C. Hybridization was followed by three post-hybridization washes in 1×SSC at room temperature and buffer exchange to 100 mM TRIS pH 7.5/150 mM NaCl. An anti-digoxigenin antibody (Fc fragment) conjugated to alkaline phosphatase (AP) was then incubated with the cells for 2–4 hr. at room temperature. After a TRIS/NaCl wash to remove unbound antibody from negative cells and exchange to the alkaline phosphatase buffer (100 mM TRIS pH 9.5/100 mM NaCl/50 mM MgCl₂), NBT/BCIP was used to develop color in those cells in which amplification had occurred. The cells were cytospun onto slides and visualized by microscopy. The human cells gave a strong calorimetric signal when the HLA-DQα exon 3 detector probe was hybridized in amplified cells. Hybridization to HLA-DQα exon 3 detector probe in unamplified cells gave a negative or a very faint but still clearly negative colorimetric response. Other negative controls included absence of amplification (i.e., no addition of SDA enzymes), absence of detector probes, and non-specific detector probe (i.e., gag or chick β-actin detector probe in amplified cells), all of which were also negative in the assay. In mouse cells alone, neither the HLA-DQα exon 3 or gag probes produced any significant color, but, when human and mouse cells were mixed during the amplification reaction, the calorimetric signal in the mouse cells was increased. However, evidence suggests that this is an artifact of the colorimetric detection system itself and that the negative cells are non-specifically taking up the dye, suggests that it is an artifact of the colorimetric detection system itself and that the negative cells are non-specifically taking up the dye.

EXAMPLE 2

Venous blood was collected in EDTA VACUTAINER™ blood collection tubes (Becton Dickinson Vacutainer Systems). DNP-conjugated anti-CD4 (L120) and biotinylated anti-CD3 (Leu 4) antibodies were added to 50 μL of whole blood and allowed to stain for 20 min. at room temperature. To lyse red blood cells, 1.0 mL of 1×FACS™ Lysing Solution (Becton Dickinson Immunocytometry Systems) was added to each tube for 10 min. The cells were fixed in 4% paraformaldehyde for 20 min. at room temperature and permeabilized by addition of 0.5 mL of 1×FACS™ Lysing Solution and 0.025% TWEEN-20. Cells were washed twice with 35 mM KPO$_4$, resuspended in 5 μL of 35 nM KPO$_4$ buffer and transferred to 0.5 mL microcentrifuge tubes.

For in situ tSDA, 40 μL of 35 mM KPO$_4$, 1.4 mM dCTPαS, 200 μM each dATP, dGTP and dTTP, 4 mM Mg acetate, 15% glycerol, 0.05 μM each bumper primer and 0.5 μM each amplification primer was added to the prepared blood sample. The samples were heated at 95° C. for 3 min. and then at 52° C. to 55° C. for 3 min. to anneal the primers. After primer annealing, 5 μL of an enzyme mix (0.5 μL 10×NEB 2 buffer, 160 units BsoBI, 8 units Bca polymerase) was added to start the amplification reaction. The tubes were incubated at 55° C. for 30 min. Amplification products were detected in situ by hybridization to fluorescein labeled detector probes. Hybridization was performed at 95° C. for 5 min., followed by 33° C. to 37° C. for 60 min. in 25 μL of SDA reaction buffer containing 100–150 ng of specific or unrelated detector probe.

Alternatively, amplification products were detected by incorporation of a fluorescein labeled signal primer during amplification. In this case, the amplification reaction buffer additionally included 100 nM of specific or unrelated 5' fluorescein labeled signal primer. The initial heating step, addition of the enzyme mixture and amplification were performed as described above.

After in situ hybridization of the detector probe, or after completion of tSDA in the presence of the signal primer, cells were washed with 1×SSC at room temperature for 30 min. Antibody staining of cell surface markers was developed with anti-DNP-phycoerythrin (PE) and Cy5/PE labeled streptavidin. Cells were washed once with 1×PBS and resuspended in 1×PBS for flow cytometric analysis. On dot plots of side scatter vs. forward scatter (SSC vs. FSC), white blood cells were shown to be unaffected by the experimental treatments. That is, cells which had undergone in situ tSDA of the HLA-DQα exon 3 target (using the primer set described above) with CD4/CD3 immunophenotyping displayed typical populations of lymphocytes, granulocytes and monocytes. The lymphocyte population also appeared normal on fluorescence dot plots of CD4 vs. CD3. These experiments demonstrated that FACS™ Lysing Solution and immunophenotyping were both compatible with in situ tSDA.

For detection of HIV by in situ tSDA, a cell line containing the HIV genome (H9+) was mixed with normal whole blood and processed as described above and gag target sequences were amplified using the selected primer set described above. Additional oligonucleotides which may be used as detector probes or signal primers were also designed for use as alternatives to SEQ ID NO:5:

AGCCACCCCACAAGATTT (SEQ ID NO:11)
GTAATACCCATGTTTTCAGCAT (SEQ ID NO:12)
AAATCTTGTGGGGTGGCT (SEQ ID NO:13)
ATGCTGAAAACATGGGTATTAC (SEQ ID NO:14)

On dot plots of SSC vs. FSC, the H9+ cells were clearly distinguishable as a population separate from lymphocytes, monocytes and granulocytes with higher forward scatter than any of the white blood cell populations. The HLA-DQα exon 3 and HIV gag targets were amplified by in situ tSDA using the primer sets described above and detected by detector probe hybridization or incorporation of a signal primer. Histogram plots of FL1 vs. cell counts are shown in FIG. 1. The HLA-DQα exon 3 positive control showed a substantial shift of peak fluorescence to the right (approximately 100 channels) as compared to negative control reactions in which no enzyme was added or unrelated probes or signal primers were used for detection. The HIV amplification reaction showed a similar fluorescence peak shift on histogram plots of FL1 vs. cell counts. These experiments confirmed that amplification was occurring in situ and demonstrated that an amplified HIV target could be detected in lysed whole blood by flow cytometry. The magnitude of the peak shifts for detector probe and signal primer detection methods was similar.

Alternatively, venous blood was collected in EDTA VACUTAINER™ blood collection tubes and PBMCs were isolated by centrifigation through FICOLL-PAQUE™. The collected cells were washed with 1×PBS, and monocytes and B cells were removed using Human T cell enrichment columns (R&D Systems). The T cell enriched fraction was stained with DNP conjugated anti-CD4 and biotinylated anti-CD3 antibody for 20 min. at room temperature. After 20 min. fixation in 4% paraformaldehyde in PBS, the cells were washed with PBS and counted. The cells were permeabilized with 10 μg/mL saponin and washed twice with 35 mM KPO$_4$. 5×10$^5$ cells were resuspended in 5 μL KPO4 buffer and transferred to 0.5 mL microcentrifuge tubes. In situ tSDA, detection of amplification products and immunophenotyping were performed as described above for the FACS™ Lysing Solution sample preparation method. The experimental results were virtually identical for the two sample preparation methods.

What is claimed is:

1. An amplification primer comprising the target binding sequence of SEQ ID NO:1, the target binding sequence of SEQ ID NO:2, the target binding sequence of SEQ ID NO:6 or the target binding sequence of SEQ ID NO:7 and, optionally a non-target biding sequence required by a selected amplification method.

2. The amplification primer of claim 1 which is an amplification primer for PRC.

3. The amplification primer of claim 1 which is an amplification primer for SDA.

4. The amplification primer of claim 1 which is an amplification primer for 3SR.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_binding
        ( B ) LOCATION: 25..42
        ( D ) OTHER INFORMATION: /standard_name= "TARGET BINDING SEQUENCE"

( i x ) FEATURE:
        ( A ) NAME/KEY: misc_feature
        ( B ) LOCATION: 19..24
        ( D ) OTHER INFORMATION: /standard_name= "RESTRICTION ENDONUCLEASE RECOGNITION SITE"

( x i ) SEQUENCE DESCRIPTION: SEQ ID NO:1:

ACCGCATCGA ATGCATGTCT CGGGTGGTAA AAGTAGTAGA AG    42

( 2 ) INFORMATION FOR SEQ ID NO:2:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_binding
        ( B ) LOCATION: 25..41
        ( D ) OTHER INFORMATION: /standard_name= "TARGET BINDING SEQUENCE"

( i x ) FEATURE:
        ( A ) NAME/KEY: misc_feature
        ( B ) LOCATION: 19..24
        ( D ) OTHER INFORMATION: /standard_name= "RESTRICTION ENDONUCLEASE RECOGNITION SITE"

( x i ) SEQUENCE DESCRIPTION: SEQ ID NO:2:

CGATTCCGCT CCAGACTTCT CGGGGTGTTT AGCATGGTGT T    41

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AAATGGTACA TCAGGCC    17

( 2 ) INFORMATION FOR SEQ ID NO:4:

( i ) SEQUENCE CHARACTERISTICS:

(A) LENGTH: 17 base pairs
                    (B) TYPE: nucleic acid
                    (C) STRANDEDNESS: single
                    (D) TOPOLOGY: linear (i i) MOLECULE TYPE: DNA (genomic)

(x i) SEQUENCE DESCRIPTION: SEQ ID NO:4:

GCAGCTTCCT CATTGAT                                                                                    17

(2) INFORMATION FOR SEQ ID NO:5:

(i) SEQUENCE CHARACTERISTICS:
                    (A) LENGTH: 20 base pairs
                    (B) TYPE: nucleic acid
                    (C) STRANDEDNESS: single
                    (D) TOPOLOGY: linear (i i) MOLECULE TYPE: DNA (genomic)

(x i) SEQUENCE DESCRIPTION: SEQ ID NO:5:

GGTGGCTCCT TCTGATAATG                                                                                 20

(2) INFORMATION FOR SEQ ID NO:6:

(i) SEQUENCE CHARACTERISTICS:
                    (A) LENGTH: 42 base pairs
                    (B) TYPE: nucleic acid
                    (C) STRANDEDNESS: single
                    (D) TOPOLOGY: linear (i i) MOLECULE TYPE: DNA (genomic)

(i x) FEATURE:
                    (A) NAME/KEY: misc_binding
                    (B) LOCATION: 25..42
                    (D) OTHER INFORMATION: /standard_name= "TARGET BINDING
                            SEQUENCE"

(i x) FEATURE:
                    (A) NAME/KEY: misc_feature
                    (B) LOCATION: 19..24
                    (D) OTHER INFORMATION: /standard_name= "RESTRICTION
                            ENDONUCLEASE RECOGNITION SITE"

(x i) SEQUENCE DESCRIPTION: SEQ ID NO:6:

ACCGCATCGA ATGCATGTCT CGGGTGGTCA ACATCACATG GC                                                        42

(2) INFORMATION FOR SEQ ID NO:7:

(i) SEQUENCE CHARACTERISTICS:
                    (A) LENGTH: 40 base pairs
                    (B) TYPE: nucleic acid
                    (C) STRANDEDNESS: single
                    (D) TOPOLOGY: linear (i i) MOLECULE TYPE: DNA (genomic)

(i x) FEATURE:
                    (A) NAME/KEY: misc_binding
                    (B) LOCATION: 25..40
                    (D) OTHER INFORMATION: /standard_name= "TARGET BINDING
                            SEQUENCE"

(i x) FEATURE:
                    (A) NAME/KEY: misc_feature
                    (B) LOCATION: 19..24
                    (D) OTHER INFORMATION: /standard_name= "RESTRICTION
                            ENDONUCLEASE RECOGNITION SITE"

(x i) SEQUENCE DESCRIPTION: SEQ ID NO:7:

CGATTCCGCT CCAGACTTCT CGGGTGAGAG GAAGCTGGTC                                                           40

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GTCTTGTGGA CAACATCTTT CC                      22

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TAACTGATCT TGAAGAAGGA ATGATC                26

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AATGGGCACT CAGTCACAGA                        20

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

AGCCACCCCA CAAGATTT                          18

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GTAATACCCA TGTTTTCAGC AT                      22

( 2 ) INFORMATION FOR SEQ ID NO:13:

( i ) SEQUENCE CHARACTERISTICS:
        ( A ) LENGTH: 18 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

AAATCTTGTG GGGTGGCT  18

(2) INFORMATION FOR SEQ ID NO:14:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

ATGCTGAAAA CATGGGTATT AC  22